US011096562B2

(12) United States Patent
Tosaka et al.

(10) Patent No.: US 11,096,562 B2
(45) Date of Patent: Aug. 24, 2021

(54) OPTICAL FIBER SCANNING SYSTEM AND ENDOSCOPE SYSTEM

(71) Applicant: OLYMPUS CORPORATION, Tokyo (JP)

(72) Inventors: Hiroshi Tosaka, Naganao (JP); Masanori Ogata, Matsumoto (JP)

(73) Assignee: OLYMPUS CORPORATION, Tokyo (JP)

( * ) Notice: Subject to any disclaimer, the term of this patent is extended or adjusted under 35 U.S.C. 154(b) by 582 days.

(21) Appl. No.: 16/045,915

(22) Filed: Jul. 26, 2018

(65) Prior Publication Data
US 2018/0353056 A1 Dec. 13, 2018

Related U.S. Application Data

(63) Continuation of application No. PCT/JP2016/052508, filed on Jan. 28, 2016.

(51) Int. Cl.
*G02B 26/08* (2006.01)
*A61B 1/00* (2006.01)
(Continued)

(52) U.S. Cl.
CPC ...... *A61B 1/00172* (2013.01); *A61B 1/00006* (2013.01); *A61B 1/00096* (2013.01);
(Continued)

(58) Field of Classification Search
CPC . A61B 1/00172; A61B 1/0638; A61B 1/0669; A61B 1/00188; A61B 1/00006;
(Continued)

(56) References Cited

U.S. PATENT DOCUMENTS

2007/0242330 A1 10/2007 Rosman et al.
2009/0015894 A1* 1/2009 Rosman ............... G02B 26/103
359/199.1

FOREIGN PATENT DOCUMENTS

EP 1 901 107 A1 3/2008
JP 2008-116922 A 5/2008
(Continued)

OTHER PUBLICATIONS

International Search Report dated Apr. 26, 2016 received in PCT/JP2016/052508.

*Primary Examiner* — Euncha P Cherry
(74) *Attorney, Agent, or Firm* — Scully, Scott, Murphy & Presser, P.C.

(57) ABSTRACT

An optical fiber scanning system includes: an optical fiber with a magnet; four drive coils configured to apply a drive magnetic field generated using a drive power signal to the magnet; four detection coils configured to output a detection signal in response to variation of a magnetic field; a controller configured to perform feedback control of the drive power signal; a signal output circuit configured to output a drive signal; a voltage-current conversion circuit configured to convert the drive signal to the drive power signal; and a correction circuit configured to output a magnet magnetic field signal by removing the drive magnetic field signal from the detection signal, and the controller controls the signal output circuit based on the magnet magnetic field signal.

11 Claims, 13 Drawing Sheets

(51) Int. Cl.
*G02B 26/10* (2006.01)
*A61B 1/06* (2006.01)
*F21V 8/00* (2006.01)
*G02B 6/00* (2006.01)

(52) U.S. Cl.
CPC ...... *A61B 1/00165* (2013.01); *A61B 1/00188* (2013.01); *A61B 1/0638* (2013.01); *A61B 1/0669* (2013.01); *G02B 6/0008* (2013.01); *G02B 26/10* (2013.01); *G02B 26/103* (2013.01); *G02B 2006/0098* (2013.01)

(58) Field of Classification Search
CPC ............ A61B 1/00096; A61B 1/00165; G02B 6/0008; G02B 26/103; G02B 26/10; G02B 2006/0098
USPC ...................................... 359/200.7
See application file for complete search history.

(56) References Cited

FOREIGN PATENT DOCUMENTS

| | | |
|---|---|---|
| JP | 2008-514970 A | 5/2008 |
| JP | 2014-81484 A | 5/2014 |
| JP | 2015-211761 A | 11/2015 |
| WO | 2006/032106 A1 | 3/2006 |
| WO | 2014/061354 A1 | 4/2014 |
| WO | 2015/166743 A1 | 11/2015 |

* cited by examiner

OPTICAL FIBER SCANNING SYSTEM AND ENDOSCOPE SYSTEM

CROSS REFERENCE TO RELATED APPLICATION

This application is a continuation application of PCT/JP2016/052508 filed on Jan. 28, 2016, the entire contents of which are incorporated herein by this reference.

BACKGROUND OF INVENTION

1. Field of the Invention

The present invention relates to an optical fiber scanning system including an optical fiber scanning apparatus including an optical fiber on which a magnet is disposed, the optical fiber being configured to output light from a free end, drive coils configured to apply a drive magnetic field generated using a drive power signal to the magnet and detection coils configured to output a detection signal in response to variation of the magnetic field, and a control section (controller) configured to perform feedback control of the drive power signal based on the detection signal, and an endoscope system including the optical fiber scanning apparatus in a rigid distal end portion of an insertion portion of an endoscope.

2. Description of the Related Art

An image pickup apparatus using an image pickup device such as a CCD or CMOS image sensor simultaneously receives reflected light from a subject by a multitude of light-receiving elements arranged in a matrix to acquire an image of the subject. In the case of an endoscope configured to perform shooting inside a human body, which is dark, an image of a range illuminated by light from a light source is acquired.

On the other hand, an image pickup apparatus including an optical fiber scanning apparatus sequentially receives reflected light from a subject by one light-receiving element while subjecting the subject to scanning irradiation with a light spot and creates an image of the subject based on data of the received light.

Japanese Patent Application Laid-Open Publication No. 2008-116922 discloses an optical fiber scanning apparatus using magnetism. In the optical fiber scanning apparatus, an optical fiber on which a magnet is disposed is arranged along a center axis of a magnetic field generating unit including a drive coil and a sensor coil arranged so as to face each other inside a cylinder. A state of vibration of the magnet, that is, a state of scanning of the optical fiber, is detected based on variation of a magnetic field detected by the sensor coil and feedback control of a drive signal for the drive coil is performed.

Also, Japanese Patent Application Laid-Open Publication No. 2014-81484 discloses an optical fiber scanning apparatus including drive coils each formed of a planar spiral coil formed on a substrate.

SUMMARY OF THE INVENTION

An optical fiber scanning system according to an embodiment includes an optical fiber scanning apparatus and a drive unit, and the optical fiber scanning apparatus includes an optical fiber on which a magnet is disposed, the optical fiber being arranged along a center axis of a tubular casing and configured to output light from a free end, four drive coils configured to apply a drive magnetic field generated using an inputted drive power signal to the magnet to drive the free end of the optical fiber and four detection coils configured to output a detection signal that is an induced electromotive force signal in response to variation of a magnetic field, the drive unit includes a signal output circuit configured to output a drive signal subjected to voltage control, a voltage-current conversion circuit configured to convert the drive signal to the drive power signal subjected to current control and output the drive power signal, a controller configured to perform feedback control of the drive power signal and a correction circuit configured to output a magnet magnetic field signal in response to variation of a magnet magnetic field due to movement of the magnet, by removing a drive magnetic field signal in response to variation of the drive magnetic field, from the detection signal, four coil sets each including any of the drive coils and any of the detection coils are disposed at respective positions that are rotationally symmetric with respect to the optical fiber, the correction circuit outputs the magnet magnetic field signal by removing the drive magnetic field signal from the detection signal, and the controller is configured to control the signal output circuit based on the magnet magnetic field signal.

An endoscope system according to another embodiment includes an optical fiber scanning apparatus of an optical fiber scanning system in an endoscope, and the optical fiber scanning system includes an optical fiber scanning apparatus and a drive unit, the optical fiber scanning apparatus includes an optical fiber on which a magnet is disposed, the optical fiber being arranged along a center axis of a tubular casing and configured to output light from a free end, four drive coils configured to apply a drive magnetic field generated using an inputted drive power signal to the magnet to drive the free end of the optical fiber and four detection coils configured to output a detection signal that is an induced electromotive force signal in response to variation of a magnetic field, the drive unit includes a signal output circuit configured to output a drive signal subjected to voltage control, a voltage-current conversion circuit configured to convert the drive signal to the drive power signal subjected to current control and output the drive power signal, a controller configured to perform feedback control of the drive power signal and a correction circuit configured to output a magnet magnetic field signal in response to variation of a magnet magnetic field due to movement of the magnet, by removing a drive magnetic field signal in response to variation of the drive magnetic field, from the detection signal, four coil sets each including any of the drive coils and any of the detection coils are disposed at respective positions that are rotationally symmetric with respect to the optical fiber, the correction circuit outputs the magnet magnetic field signal by removing the drive magnetic field signal from the detection signal, and the controller is configured to control the signal output circuit based on the magnet magnetic field signal.

DETAILED DESCRIPTION OF THE PREFERRED EMBODIMENTS

First Embodiment

Figure 1:
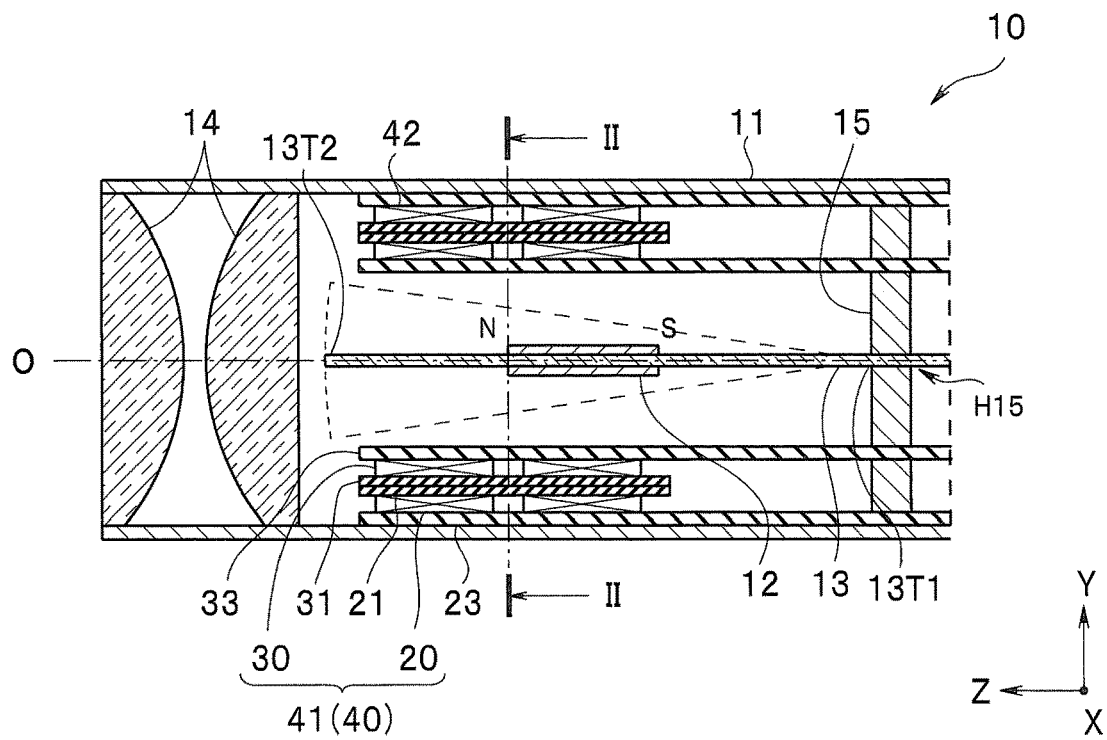
FIG. 1 is a cross-sectional view along a center axis of an optical fiber scanning apparatus in an optical fiber scanning system according to a first embodiment.

First, an optical fiber scanning apparatus 10 in an optical fiber scanning system 1 according to the present embodiment will be described. It should be noted that each of the drawings based on respective embodiments in the description below are schematic ones; and e.g., a relationship between a thickness and a width of each part and ratios of thicknesses among the respective parts are different from actual ones, and parts that are different in dimensional relationship and ratio depending on the drawings may be included in the drawings. Also, illustration of, or provision of reference numerals to, some of components may be omitted.

Figure 2:
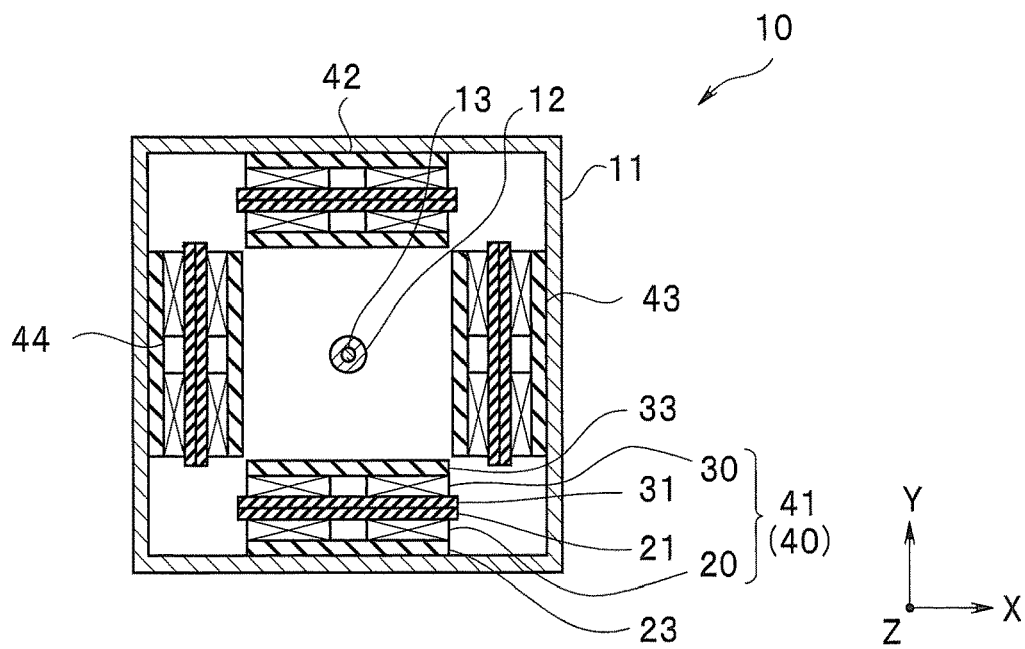
FIG. 2 is a cross-sectional view, along line II-II in FIG. 1, of the optical fiber scanning apparatus in the optical fiber scanning system according to the first embodiment.

As illustrated in FIGS. 1 and 2, the optical fiber scanning apparatus 10 includes a tubular casing 11, an optical fiber 13, a magnet 12 disposed on the optical fiber 13, coil sets 41 to 44 and an illumination optical system 14. The optical fiber 13 is arranged along a center axis O (Z-axis direction) of the casing 11.

The casing 11 is formed of a non-magnetic metal such as aluminum or resin. The tubular casing 11 includes a hollow part having a square shape in a cross-section perpendicular to the center axis O (X-Y plane). For example, the casing 11 has an outer diameter of 1 mm or more and 10 mm or less and a wall thickness of 10 μm or more and 1000 μm or less. The casing may have a rectangular parallelepiped shape including an outer face including corner parts subjected to rounding/chamfering or a cylindrical shape.

The optical fiber 13 guides light from a light source unit (not illustrated) and outputs the illuminating light from a free end 13T2. A subject is subjected to spot irradiation with the illuminating light via the illumination optical system 14 including a plurality of lenses.

For example, the magnet 12, which is formed of an Sm—Co alloy, has a tubular shape and is magnetized in a long axis direction (optical axis direction: Z-axis direction). The optical fiber 13 is inserted through and bonded to a through-hole H15 of a holding member (ferrule) 15. The free end 13T2 of the optical fiber 13 in a cantilevered state in which the part bonded with the holding member 15 (fixed end 13T1) is fixed is movable upward, downward, rightward and leftward within the X-Y plane with the fixed end 13T1 as a base point.

Four coil sets 41 to 44 are disposed at respective positions that are rotationally symmetric with respect to the optical fiber 13 inside the casing 11. Below, each of the coil sets 41 to 44 may be referred to as "coil set 40".

Figure 3:
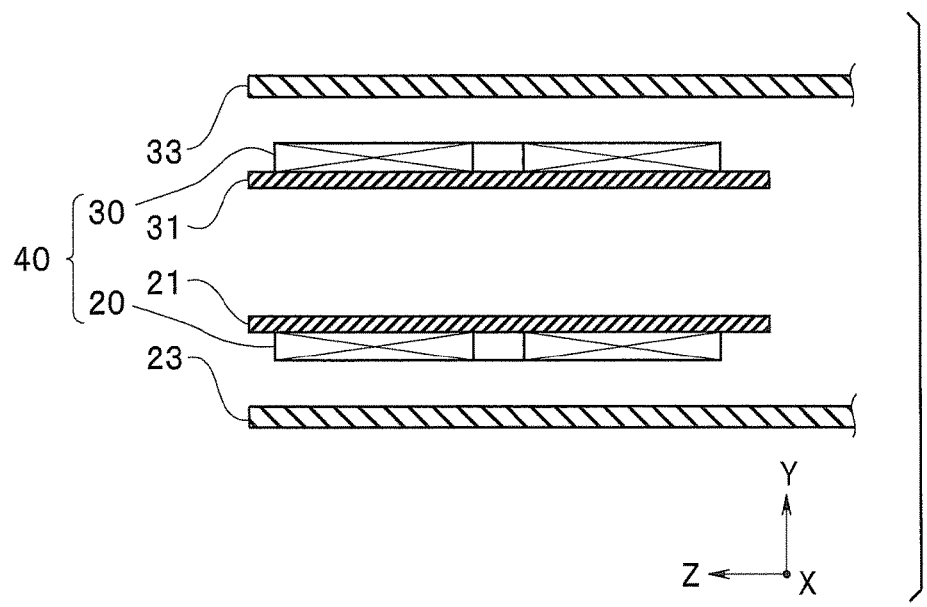
FIG. 3 is an exploded view of a coil set in the optical fiber scanning system according to the first embodiment.
Figure 4A:
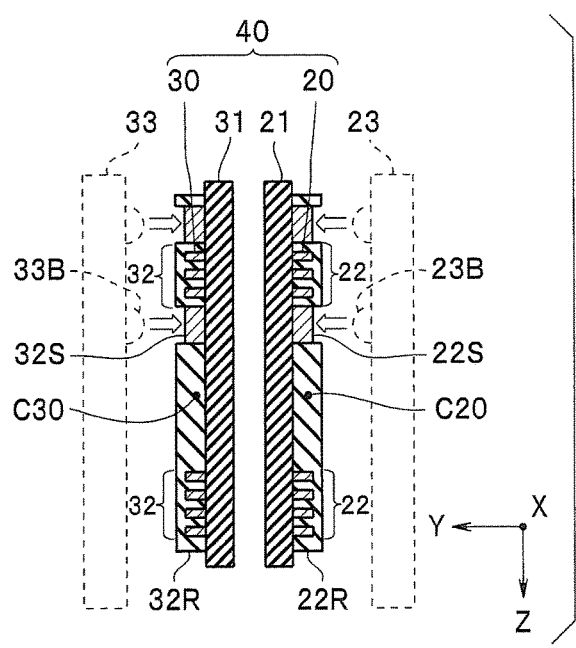
FIG. 4A is an exploded view of a coil set in the optical fiber scanning system according to the first embodiment.
Figure 4B:
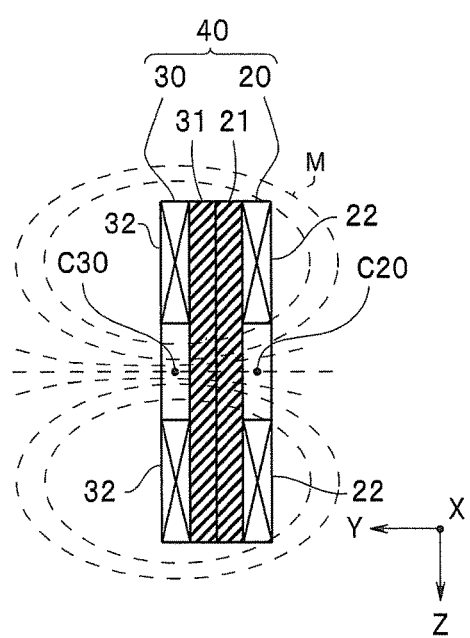
FIG. 4B is a cross-sectional view of a coil set in the optical fiber scanning system according to the first embodiment.

As illustrated in FIGS. 3, 4A and 4B, each coil set 40 includes a detection coil 20 and a drive coil 30, which are stacked on each other. Each of the detection coil 20 and the drive coil 30 is a planar spiral coil formed of a planarly-wound thin-film conductor.

Figure 5:
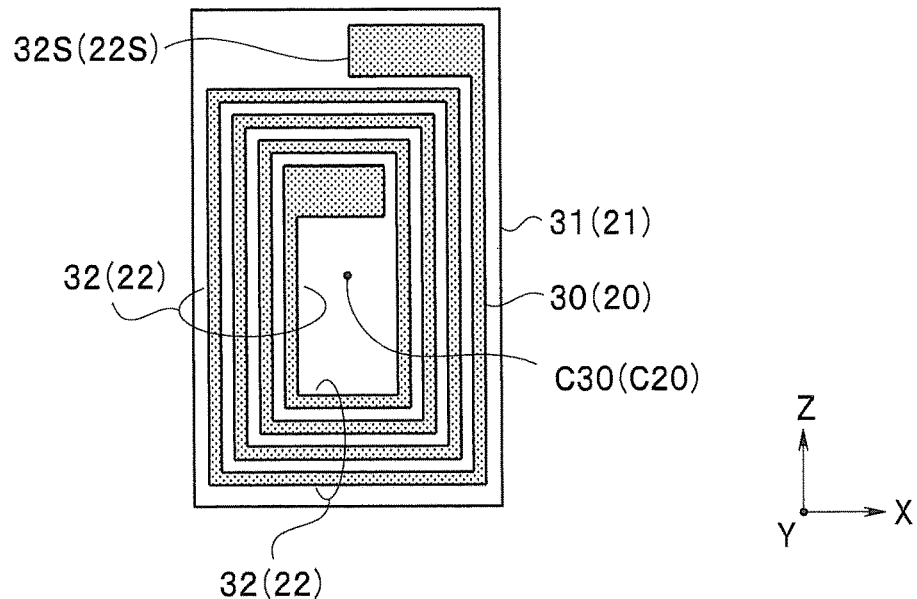
FIG. 5 is a top view of a drive coil (detection coil) in the optical fiber scanning system according to the first embodiment.

As illustrated in FIG. 5, each drive coil 30 disposed on a relevant first coil substrate 31 includes an electrode pad 32S at each of opposite end parts of a winding portion 32.

A planar spiral coil is fabricated by means of patterning according to, e.g., an additive method or a subtractive method using, for example, a high-precision resist mask fabricated by means of a photolithographic method using a photoresist and a photo mask. In the additive method, for example, a thin film of conductor is formed in a pattern by means of a copper plating method. In the subtractive method, a conductor film is patterned by means of etching.

For example, the winding portion 32 of each spiral-shaped drive coil 30 disposed on the relevant first coil substrate 31 formed of silicon, via an insulation layer (not illustrated) formed of, e.g., silicon oxide, is covered by an insulation layer 32R formed of a resin such as polyimide or epoxy. A contact hole is provided in parts of the insulation layer 32R over the electrode pads 32S.

Here, in each drive coil 30, an electrode pad 32S is also arranged on a center part of the relevant winding portion 32. In order to provide an electrode pad 32S in the periphery of the winding portion 32, the drive coil 30 may further include one additional insulation layer/lead wiring or may be a multi-layer coil in which multiple planar coils are stacked via an insulation layer as described later.

The electrode pads 32S of the drive coil 30 are solder-bonded to bumps 33B of a first wiring board 33.

As illustrated in FIG. 4B, upon reception of a drive power signal via the first wiring board 33, a drive coil 30 generates a magnetic field M (see FIG. 4B) in a direction perpendicular to the plane of the coil. The magnetic field M generated by the drive coil 30, which is a spiral coil, is largest at a center C30 of winding portion 32.

The detection coils 20 each have a configuration similar to the configuration of the drive coils 30. In other words, each detection coil 20 disposed on a relevant second coil substrate 21 includes an electrode pad 22S at each of opposite end parts. The electrode pads 22S of each detection coil 20 are solder-bonded to bumps 23B of a relevant second wiring board 23.

When a magnetic field varies, a detection coil 20 outputs an induced electromotive force signal in response to the variation. The induced electromotive force signal is transmitted via the relevant second wiring board 23.

Here, the detection coils 20 may each have a configuration that is different from the configuration of the drive coils 30. In other words, the detection coils 20 do not receive a large amount of power unlike the drive coils 30. Therefore, each of the detection coils 20 may be an aluminum thin-film pattern that is formed of, for example, a copper plating film, having electrical resistance that is larger than electrical resistance of the drive coils 30, and is disposed by means of, for example, a sputtering method. Also, for detection sensitivity enhancement, the number of turns of each detection coil 20 is preferably larger than the number of turns of each drive coil 30.

In the optical fiber scanning apparatus 10, each coil set 40 is configured by a first wiring board 33, a drive coil 30, a first coil substrate 31, a second coil substrate 21, a detection coil 20 and a second wiring board 23 being stacked sequentially.

FIG. 4B illustrates an example in which a configuration of a coil set 40, the configuration being the same as the configuration in FIG. 4A, is illustrated in a simplified manner. For example, a winding portion 32, etc., are simplified and a center C30 of the winding portion 32 is illustrated as a center of a drive coil 30. Also, in FIGS. 1 to 3 already used for description, the coil sets 40 are illustrated in a simplified manner.

The drive coil 30 and the detection coil 20 are stacked on each other so that respective centers C30, C20 substantially coincide with each other, and a coil substrate 31 and a coil substrate 21 are bonded to each other to form a coil set 40, that is, a drive coil 30 and a detection coil 20 are stacked so as to overlap each other.

In the optical fiber scanning apparatus 10, in order to reduce drive power signal strength, each coil set 40 is arranged so that the relevant drive coil 30 is positioned on the center (inner) side of the casing 11. However, each coil set 40 may be arranged so that the relevant detection coil 20 is positioned on the center side of the casing 11.

As already described, upon receipt of a drive power signal, a drive coil 30 generates a magnetic field M in a direction perpendicular to the plane of the coil. An intensity of the magnetic field M is set according to, e.g., a current value of the drive power signal and the number of winds (turns) of the spiral coil. If a direction of the drive power signal flowing through the coil is reversed, a direction of the magnetic field generated is reversed.

As illustrated in FIG. 2, in the optical fiber scanning apparatus 10, the four coil sets 41 to 44 are arranged at the respective rotationally symmetric positions. In other words, the first coil set 41 and the second coil set 42 are arranged at mutually facing positions, and the third coil set 43 and the fourth coil set 44 are arranged at mutually facing positions.

Therefore, the drive coils 30 of the coil set 41 and the coil set 42 generate a magnetic field in a Y-axis direction, and the drive coils 30 of the coil set 43 and the coil set 44 generate a magnetic field in an X-axis direction.

The optical fiber 13 (magnet 12) is arranged at an equal distance from the four drive coils 30, that is, a center of the hollow part of the casing 11.

Next, a method for driving the optical fiber scanning apparatus 10 will be briefly described.

When a drive power signal is supplied to the coil set 41 (drive coil 30), for example, a magnetic field, the N-pole of which is arranged in the inner side of the coil set 41, is generated. Simultaneously, when the drive power signal is supplied to the coil set 42, for example, a magnetic field, the S pole of which is arranged on the inner side of the coil set 42, is generated. In other words, the coil set 41 and the coil set 42 arranged so as to face each other generate magnetic fields having different magnetic poles on the inner sides of the coil set 41 and the coil set 42.

Therefore, for example, a front-side N-pole end of the magnet 12 arranged in the magnetic fields is drawn upward on the Y-axis. Thus, the free end 13T2 of the optical fiber 13 also moves upward on the Y-axis.

On the other hand, when a drive power signal in a direction opposite to the direction of the above drive power signal is supplied to the coil set 41, a magnetic field, the S pole of which is arranged on the inner side of the coil set 41, is generated. Then, the N-pole end of the magnet 12 is drawn downward on the Y-axis. Thus, the free end of the optical fiber 13 also moves downward on the Y-axis.

As a result of control of the direction of a drive power signal supplied to the coil sets 41, 42, that is, supply of a drive power signal Iy, which is an alternating current signal subjected to current control, the free end of the optical fiber 13 vibrates and thus scans in the Y-axis direction. Likewise, as a result of control of a direction of a drive power signal Ix supplied to the coil sets 43, 44, the free end of the optical fiber 13 scans in the X-axis direction orthogonal to the Y-axis direction.

As a result of control of the directions of drive power signals supplied to the four coil sets 41 to 44, the free end of the optical fiber 13 two-dimensionally scans within the X-Y plane. Consequently, a light spot outputted from the free end of the optical fiber 13 scans two-dimensionally. A width of the scanning is controlled according to the strengths of the drive power signals.

For a method of the two-dimensional scanning, a spiral scanning method, a raster scanning method or a Lissajous method is preferable because image processing is easy.

Also, the magnet 12 and the coil sets 40 may be arranged so that drive magnetic fields are applied to the rear side of the magnet 12.

Figure 6:
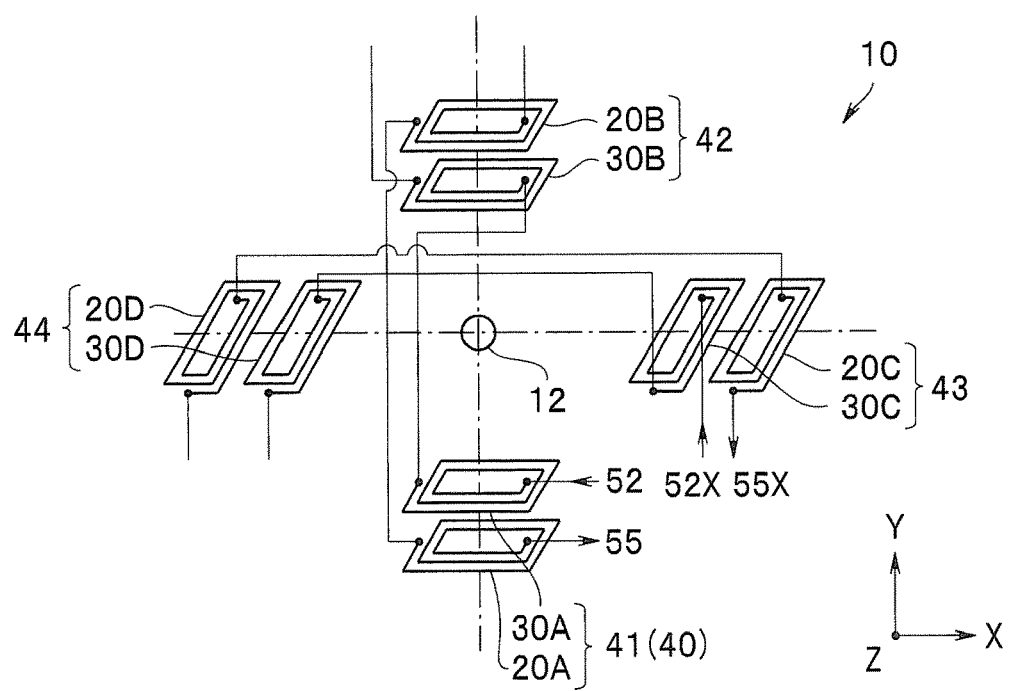
FIG. 6 is a diagram of connections of coil sets in the optical fiber scanning system according to the first embodiment.

As illustrated in FIG. 6, drive coils of two coil sets arranged so as to face each other are serially connected. For example, a drive coil 30A of the first coil set 41 and a drive coil 30B of the second coil set 42 are serially connected. Also, detection coils of two coil sets arranged so as to face each other are serially connected. For example, a detection coil 20A of the first coil set 41 and a detection coil 20B of the second coil set 42 are serially connected.

In the serial connection between the drive coil 30A and the drive coil 30B arranged so as to face each other, for example, an electrode pad 32S in an outer peripheral part of the drive coil 30A and an electrode pad 32S in a center part of the drive coil 30B are connected so that directions of magnetic fields generated are the same. A drive power signal is inputted to an electrode pad 32S in an inner peripheral part of the drive coil 30A from a voltage-current conversion section 52 (see FIG. 7).

On the other hand, in the serial connection between the detection coil 20A and the detection coil 20B arranged so as to face each other, for example, an electrode pad 22S in an outer peripheral part of the detection coil 20A and an electrode pad 22S in an outer peripheral part of the detection coil 20B are connected so that detection signals outputted by the two detection coils 20 are added up and outputted as an added-up detection signal. The detection signal (added-up detection signal) outputted from an electrode pad 22S in an inner peripheral part of the detection coil 20A is inputted to an arithmetic section (arithmetic circuit) 55 (see FIG. 7) of a correction section (correction circuit) 54.

A drive coil 30C of the third coil set 43 and a drive coil 30D of the fourth coil set 44 are serially connected. Also, a detection coil 20C of the third coil set 43 and a detection coil 20D of the fourth coil set 44 are serially connected. A drive power signal is inputted to the drive coil 30C from a voltage-current conversion section (voltage-current conversion circuit) 52X (see FIG. 7), and the detection coil 20C outputs a detection signal to an arithmetic section 55X (see FIG. 7) of a correction section 54X.

Figure 7:
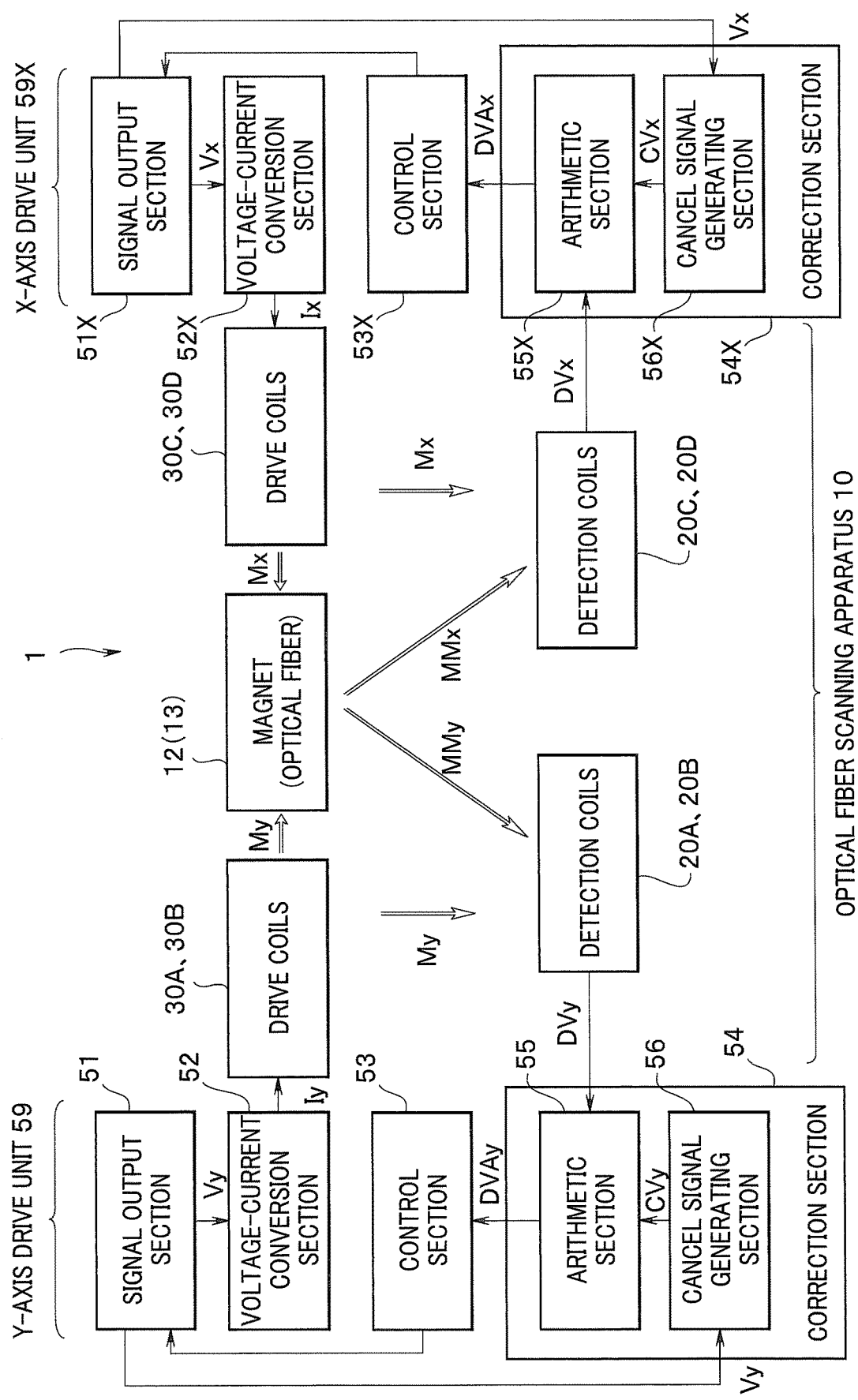
FIG. 7 is a diagram of a configuration of the optical fiber scanning system according to the first embodiment.

As illustrated in FIG. 7, the optical fiber scanning system 1 according to the embodiment includes the optical fiber scanning apparatus 10, and drive units 59(59X), which are drive apparatuses. The optical fiber scanning apparatus 10 includes the optical fiber 13 on which the magnet 12 is disposed, the drive coils 30A to 30D and the detection coils 20A to 20D. The drive units 59(59X) include signal output sections (signal output circuits) 51, 51X, voltage-current conversion sections (voltage-current conversion circuit) 52, 52X, control sections (controllers) 53, 53X and correction sections (correction circuits) 54, 54X, respectively.

The description will be now given mainly on, e.g., a control unit (Y-axis drive unit 59) for the first coil set 41 and the second coil set 42 that generate a drive magnetic field My in the Y-axis direction; however, the same applies to a control unit (X-axis drive unit 59X) for the third coil set 43 and the fourth coil set 44 that generate a drive magnetic field Mx in the X-axis direction.

Figure 8:
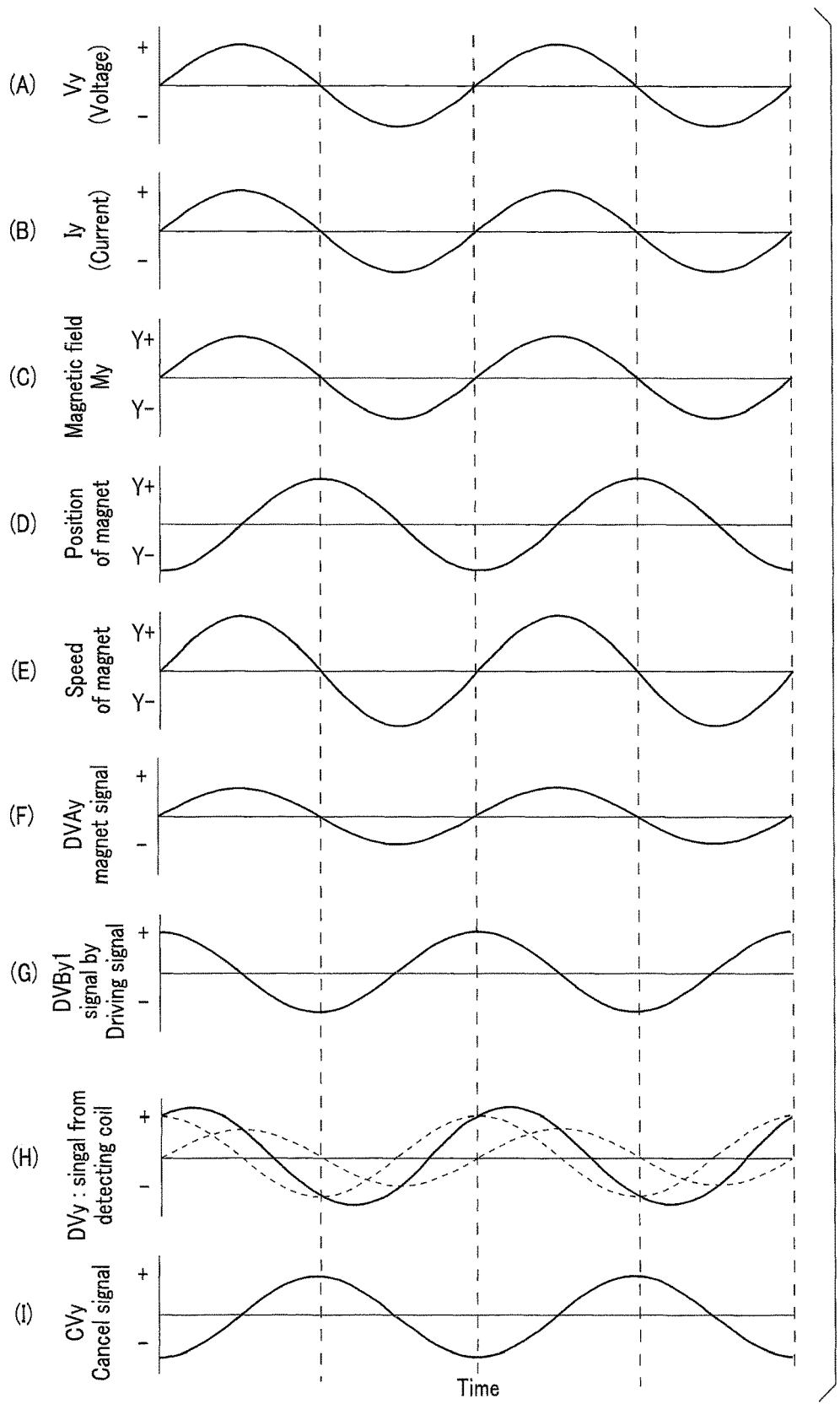
FIG. 8 is a diagram illustrating, e.g., signal waveforms in the optical fiber scanning system according to the first embodiment.

The signal output section 51 is, for example, a function generator and outputs a voltage-controlled Y-axis direction drive signal Vy. As illustrated in FIG. 8(A), in the optical fiber scanning system 1, the drive signal Vy is a sine-wave alternating current signal. The voltage-current conversion section 52 converts the drive signal Vy to a current-controlled drive power signal Iy indicated in FIG. 8(B) and outputs the drive power signal Iy. The drive signal Vy is a voltage signal. The drive power signal Iy is a current signal.

The drive coils 30A, 30B generate a drive magnetic field My parallel to the Y-axis, which is indicated in FIG. 8(C), in response to the drive power signal Iy inputted from the voltage-current conversion section 52. When the drive magnetic field My is applied, the magnet 12 vibrates in the Y-axis direction as indicated in FIGS. 8(D) and 8(E). In other words, the free end 13T2 of the optical fiber 13 on which the magnet 12 is disposed is driven in the Y-axis direction, and light outputted from the free end 13T2 is made to scan in the Y-axis direction.

If a frequency of the drive magnetic field My is a resonant frequency fR of the cantilevered optical fiber 13, the vibration of the magnet 12, that is, the vibration of the optical fiber 13 is a differentiated signal of the drive magnetic field My.

The detection coils 20A, 20B output a detection signal DVy indicated in FIG. 8(H). A detection signal DV is an induced electromotive force signal in response to variation of a magnetic field M, more exactly, a speed of variation of a magnetic field M, that is, a differentiated signal of a signal of a magnetic field M (magnetic field signal). Where the magnetic field signal is a sine-wave signal, the detection signal DV is a cosine-wave signal, a phase of which is shifted by $(\pi/2)$.

Here, as illustrated in FIG. 8(H), for example, a drive magnetic field signal DVBy1 according to a speed of variation of the Y-axis direction drive magnetic field My, which is indicated in FIG. 8(G), and a magnet magnetic field signal DVAy according to a speed of variation of a magnet magnetic field MMy due to Y-axis direction vibration of the magnet 12, which is indicated in FIG. 8(F), are superimposed on the detection signal DVy. Thus, the magnet magnetic field signal DVAy cannot be obtained unless the drive magnetic field signal DVBy1 is removed from the detection signal DVy. In other words, a cancel signal CVy corresponding to the drive magnetic field signal DVBy1 contained in the detection signal DVy, which is illustrated in FIG. 8(I), is necessary.

In other words, an induced electromotive force necessary for detecting a state of scanning of the optical fiber scanning apparatus 1 is an induced electromotive force according to vibration of the optical fiber 13, that is, the magnet magnetic field signal DVAy, and an induced electromotive force of the detection coils 20 according to the drive magnetic field My generated by the drive coils 30, that is, the drive magnetic field signal DVBy1 is not necessary. In order to cancel the unnecessary induced electromotive force (drive magnetic field signal DVBy1), a cancel signal generating section (cancel signal generating circuit) 56 is necessary.

The detection signal DVy is a small-current voltage signal and is inputted to the correction section 54 after the detection signal DVy is amplified, as needed. Also, the detection signal DVy is subjected to high-frequency noise removal by, e.g., a frequency filter (for example, a low-pass filter or a band-pass filter), as needed.

The correction section 54 includes the cancel signal generating section 56 configured to generate a cancel signal CVy, which is indicated in FIG. 8(I), and the arithmetic section (arithmetic circuit) 55 configured to output the magnet magnetic field signal DVAy indicated in FIG. 8(G) by removing the drive magnetic field signal DVBy1 from the detection signal DVy using the cancel signal CVy.

The cancel signal generating section 56 converts the drive signal Vy outputted by the signal output section 51 to the cancel signal CVy. As already described, where the drive signal Vy is a sine-wave signal, the drive magnetic field signal DVBy1, which is a differentiated signal of the drive signal Vy, is a signal that is different from the drive signal Vy only in phase. Thus, the arithmetic section 55 outputs the magnet magnetic field signal DVAy by adding the cancel signal CVy, which is the drive signal Vy subjected to amplitude adjustment, to the detection signal DVy.

In order to remove the cancel signal CVy from the detection signal DVy, the cancel signal CVy and the detection signal DVy need to be voltage signals of a same level. Since the drive signal Vy is a low-power voltage signal, the drive signal Vy can easily be converted to the cancel signal CVy, which is a low-power voltage signal of a level that is the same as the level of the detection signal DVy.

An optimum cancel signal CVy may vary depending on the optical fiber scanning system because of manufacture variations. It is preferable that the cancel signal generating section 56 be subjected to amplitude adjustment after assembly of the optical fiber scanning system 1. More specifically, the cancel signal CVy is subjected to voltage adjustment (amplitude adjustment) with, e.g., a variable resistor and thus set so that the detection signal DVy becomes zero in a state in which the magnet 12 does not move, for example, a state in which a drive power signal Iy of a frequency at which the optical fiber 13 is not driven is supplied to the drive coils 30 or a state in which the magnet 12 is fixed via a fixing tool.

Next, operation of the X-axis control unit 59X will be described. The operation of the X-axis control unit 59X is the same as the operation of the Y-axis control unit 59.

The signal output section 51X outputs a drive signal Vx. In the optical fiber scanning system 1 in which two-dimensional scanning is performed according to the raster scan method or the Lissajous scanning method, the X-axis direction drive signal Vx is different in frequency f from the Y-axis direction drive signal Vy. The voltage-current conversion section 52X converts the drive signal Vx to a drive power signal Ix and outputs the drive power signal Ix. The drive coils 30C, 30D generate an X-axis direction drive magnetic field Mx in response to the drive power signal Ix. When the drive magnetic field Mx is applied, the magnet 12 vibrates in the X-axis direction. In other words, the free end 13T2 of the optical fiber 13 on which the magnet 12 is disposed is driven in the X-axis direction, and light outputted from the free end 13T2 is made to scan in the X-axis direction.

The detection coils 20C, 20D output a detection signal DVx, which is an induced electromotive force signal in response to magnetic field variation. Here, a drive magnetic field signal DVBx1 in response to variation of the drive magnetic field Mx and a magnet magnetic field signal DVAx in response to variation of a magnet magnetic field MMx due to vibration of the magnet 12 are superimposed on the detection signal DVx.

The correction section 54X includes a cancel signal generating section 56X configured to generate a cancel signal CVx corresponding to the drive magnetic field signal DVBx1, and the arithmetic section 55X configured to output the magnet magnetic field signal DVAx by removing the drive magnetic field signal DVBx1 from the detection signal DVx using the cancel signal CVx. The control section 53X controls the signal output section 51X based on the magnet magnetic field signal DVAx.

The control section 53 and the control section 53X may be a same control section. Also, the control sections 53, 53X and the correction sections 54, 54X each may be an electronic circuit as described later or a CPU configured to operate according to a predetermined program.

For example, if an amplitude of movement (vibration) of the magnet 12 is smaller than a predetermined value, the control sections 53, 53X controls the signal output sections 51, 51X so as to increase strengths of drive power signals Iy, Ix, respectively. Therefore, the optical fiber scanning system 1 enables efficient and stable scanning irradiation.

In the optical fiber scanning system 1, the cancel signal generating sections 56, 56X convert the drive signals Vy, Vx to generate the cancel signals CVy, CVx, respectively.

It is possible to convert a drive power signal to a cancel signal. However, a drive power signal is a current-controlled high-power signal. Therefore, it is necessary to convert a drive power signal to a voltage signal suitable for control and further convert the voltage signal to a cancel signal of a level that is the same as a level of a detection signal. In addition, conversion of a high-power drive power signal to a low-power cancel signal is energy consuming.

On the other hand, as already described, in the optical fiber scanning system 1, a drive signal is a low-power voltage signal and thus can be converted to a cancel signal, which is a low-power voltage signal of a level that is the same as a level of a detection signal, directly, that is, without current/voltage conversion. In a manufacturing process, an optimum cancel signal can be generated efficiently merely by adjusting an amplitude of a voltage-controlled drive signal.

Furthermore, in the optical fiber scanning system 1 in which the detection coils 20 and the drive coils 30 are planar spiral coils, two detection coils 20 having a same configuration can be arranged at mutually-facing positions. A detection signal, that is, an induced electromotive force signal outputted by two detection coils 20 serially connected is twice a detection signal outputted by one detection coil 20 in size. Furthermore, a magnitude of a detection signal outputted by one detection coil 20 is increased/decreased according to a distance between the magnet 12 and the detection coil 20 even though a speed of movement of the magnet 12 is the same. On the other hand, a magnitude of a detection signal outputted by two detection coils 20 serially connected and arranged so as to face each other is proportional to the speed of movement of the magnet 12 because the detection signal is a sum of the detection signals of the two detection coils 20. Thus, control of the optical fiber scanning system 1 is easy.

Also, in the optical fiber scanning system 1, each of the drive coils 30 and the detection coils 20 is a planar spiral coil. Thus, the optical fiber scanning apparatus 10 in the optical fiber scanning system 1 has a diameter that is smaller than a diameter of a conventional optical fiber scanning apparatus including bulk magnetic bodies and bulk conductors. Furthermore, in the optical fiber scanning apparatus 10, coil sets 40 each including a drive coil 30 and a detection coil 20 stacked on each other can be arranged at mutually facing positions. The optical fiber scanning apparatus 10 in the optical fiber scanning system 1 enables a magnetic field to be applied to the magnet 12 from each of drive coils on the opposite sides, and thus, has a good drive efficiency relative to a conventional optical fiber scanning apparatus in which a drive coil can be arranged only on one side.

The four coil sets 41 to 44 are not essential components of the optical fiber scanning system 1. For example, an optical fiber scanning system including two coil sets 41, 43 arranged orthogonal to each other also enables two-dimensional scanning. Also, an optical fiber scanning system including one coil set 41 enables one-dimensional scanning.

Modifications of First Embodiment

Next, optical fiber scanning systems 1A to 1C according to modifications of the first embodiment will be described. The optical fiber scanning systems 1A to 1C according to the modifications are similar to the optical fiber scanning system 1 and have effects that are the same as the effects of the optical fiber scanning system 1, and thus, components having functions that are the same as the functions of components in the optical fiber scanning system 1 are provided with reference numerals that are the same as reference numerals of the components in the optical fiber scanning system 1 and description of such components will be omitted.

Modification 1 of First Embodiment

Figure 9:
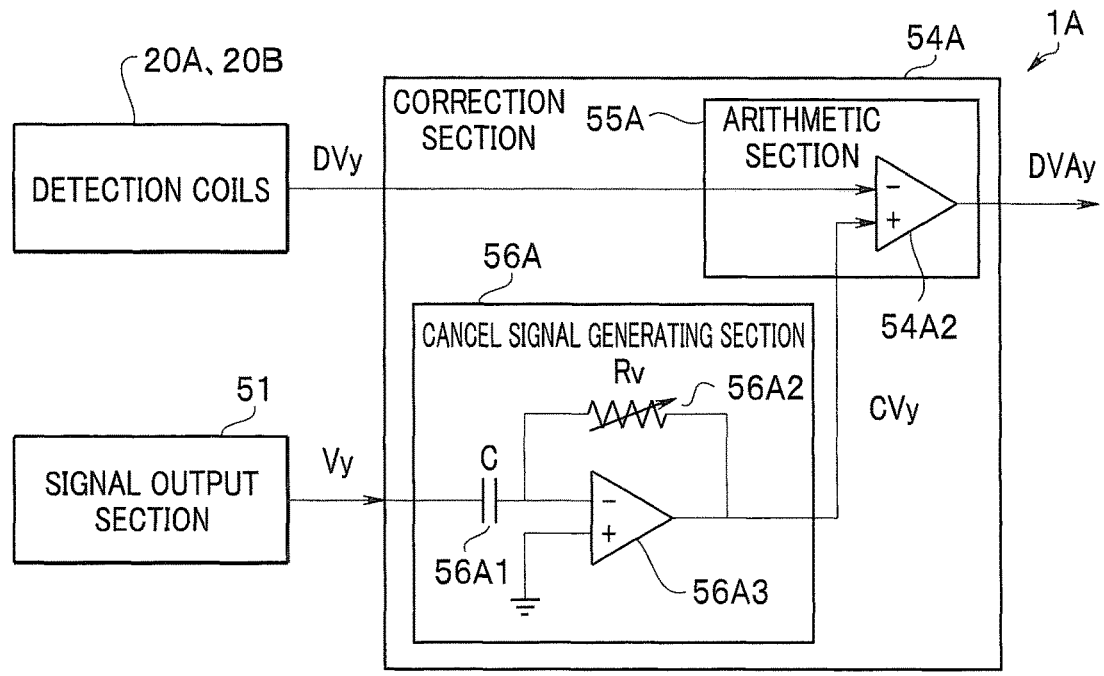
FIG. 9 is a diagram of a configuration of a correction section in an optical fiber scanning system according to modification 1 of the first embodiment.

As illustrated in FIG. 9, a correction section 54A in an optical fiber scanning system 1A according to modification 1 includes a cancel signal generating section 56A, and an arithmetic section 55A including a differential amplifier 54A2.

The cancel signal generating section 56A includes a capacitor 56A1, a variable resistor 56A2 and a differential amplifier 56A3. In other words, the cancel signal generating section 56A includes a differentiation circuit and a voltage adjustment circuit. The arithmetic section 55A includes a differential amplifier. A drive signal Vy is subjected to differentiation and voltage (amplitude) adjustment and thus converted to a cancel signal CVy by the cancel signal generating section 56A. Then, a difference between the cancel signal CVy and a detection signal DVy obtained by the differential amplifier 56A2 is outputted as a magnet magnetic field signal DVAy from the arithmetic section 55A.

The optical fiber scanning system 1A has effects that are the same as the effects of the optical fiber scanning system 1. Furthermore, the cancel signal generating section 56A includes a differentiation circuit and thus, the optical fiber scanning system 1A is applicable also to a case where a drive signal is not of a sine wave.

Modification 2 of First Embodiment

Figure 10:
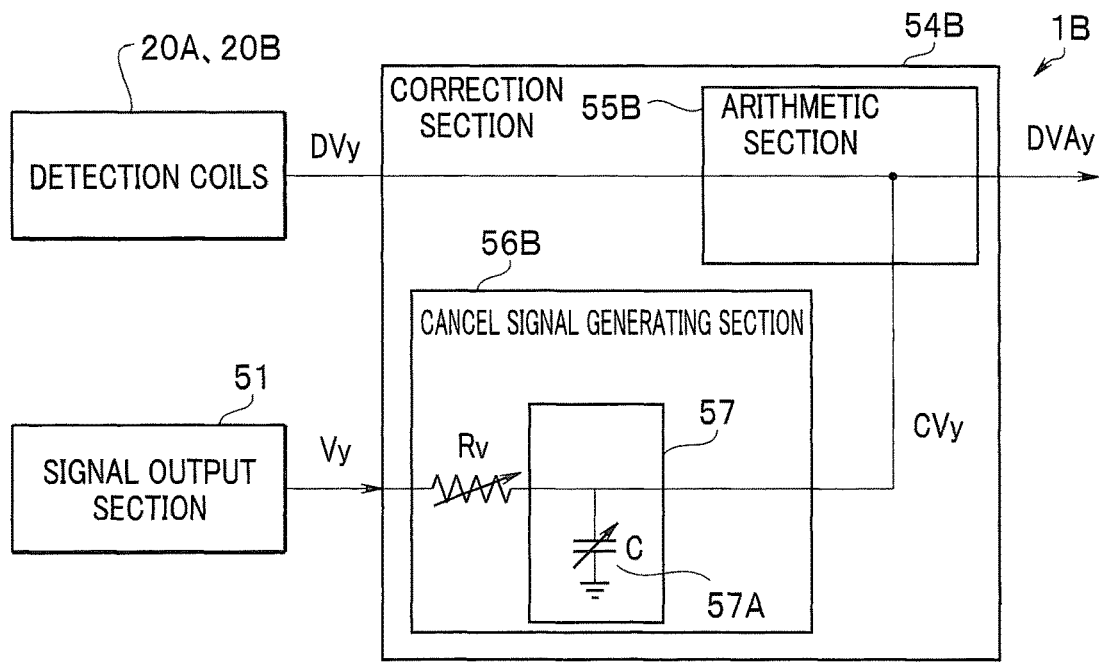
FIG. 10 is a diagram of a configuration of a correction section in an optical fiber scanning system according to modification 2 of the first embodiment.

As illustrated in FIG. 10, a correction section MB in an optical fiber scanning system 1B according to modification 2 includes a cancel signal generating section 56B, and an arithmetic section 55B configured to add up a cancel signal CVy and a detection signal DVy. The cancel signal generating section 56B includes a phase adjustment section (phase adjustment circuit) 57 configured to generate a phase-adjusted cancel signal.

As already described, in principle, a phase of a drive magnetic field signal DVBx1 is shifted by $(\pi/2)$ from a phase of a drive signal Vy. However, in an actual system, the phase shift may not be $(\pi/2)$ because of, e.g., inter-wiring-inductance, stray capacitance and/or a processing speed. Also, if a frequency f of a drive magnetic field My is larger than a resonant frequency fR of a cantilevered optical fiber 13, the phase shift is $((\pi/2)+\alpha)$, and if a frequency f of a drive magnetic field My is smaller than the resonant frequency fR of the cantilevered optical fiber 13, the phase shift is $((\pi/2)-\beta)$ (each of $\alpha$ and $\beta$ is a positive number). In such cases, even if feedback control is performed, desired optical fiber scanning cannot be achieved.

The phase adjustment section 57 delays the phase by a capacitor 57A. In order to advance the phase, a phase adjustment section including an inductor instead of the capacitor 57A is used.

Here, since an amplitude of the cancel signal CVy becomes small as a result of phase adjustment, it is preferable that the correction section MB include an amplification circuit.

In the optical fiber scanning system 1B, even if a phase shift of the drive magnetic field signal DVBx1 relative to the drive signal Vy is not $(\pi/2)$, the phase is adjusted by the correction section MB, and thus, an optimum cancel signal CVy can be generated.

Modification 3 of First Embodiment

Figure 11:
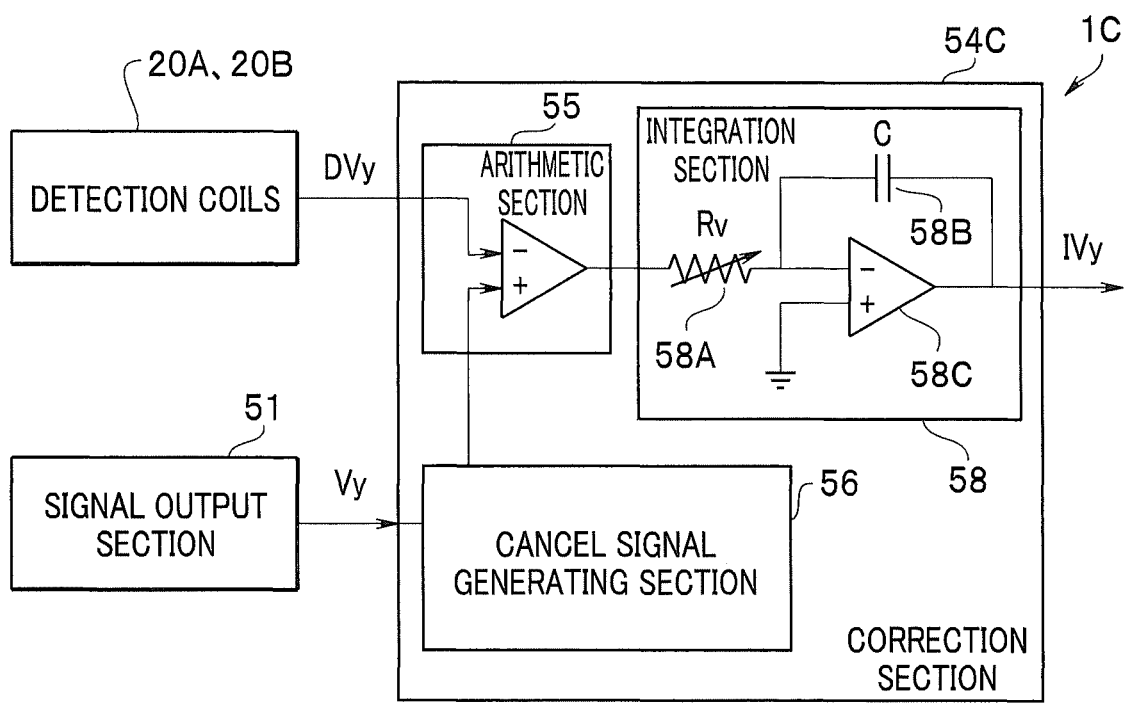
FIG. 11 is a diagram of a configuration of a correction section in an optical fiber scanning system according to modification 3 of the first embodiment.

As illustrated in FIG. 11, a correction section MC in an optical fiber scanning system 1C according to modification 3 includes an integration section (integration circuit) 58 configured to integrate a magnet magnetic field signal to output a position signal indicating a position of a magnet 12.

The integration section 58 includes a variable resistor 58A, a capacitor 58B and a differential amplifier 58C. The correction section 54C integrates a magnet magnetic field signal DVAy, which is information indicating a movement speed (vibration speed) of the magnet 12, and outputs a position information signal IVy for the magnet 12, the position information signal IVy more facilitating control by a control section 53. Likewise, an X-axis drive unit 59X includes an integration section and a signal output section 51X is controlled according to a position information signal IVx.

The integration section 58, etc., may be included in, e.g., the control section 53 or may be a functional section provided by a program executed by a control section formed of a CPU.

Second Embodiment

Next, an optical fiber scanning system 1D according to a second embodiment will be described. The optical fiber scanning system 1D is similar to the optical fiber scanning system 1 and has effects that are the same as the effects of the optical fiber scanning system 1, and thus, components having functions that are the same as the functions of components in the optical fiber scanning system 1 are provided with reference numerals that are the same as reference numerals of the components in the optical fiber scanning system 1 and description of such components will be omitted. Also, as described later, in FIG. 12, illustration of components of an X-axis drive unit 59X, components having no direct relationship with operation of a Y-axis drive unit 59, is omitted.

Figure 12:
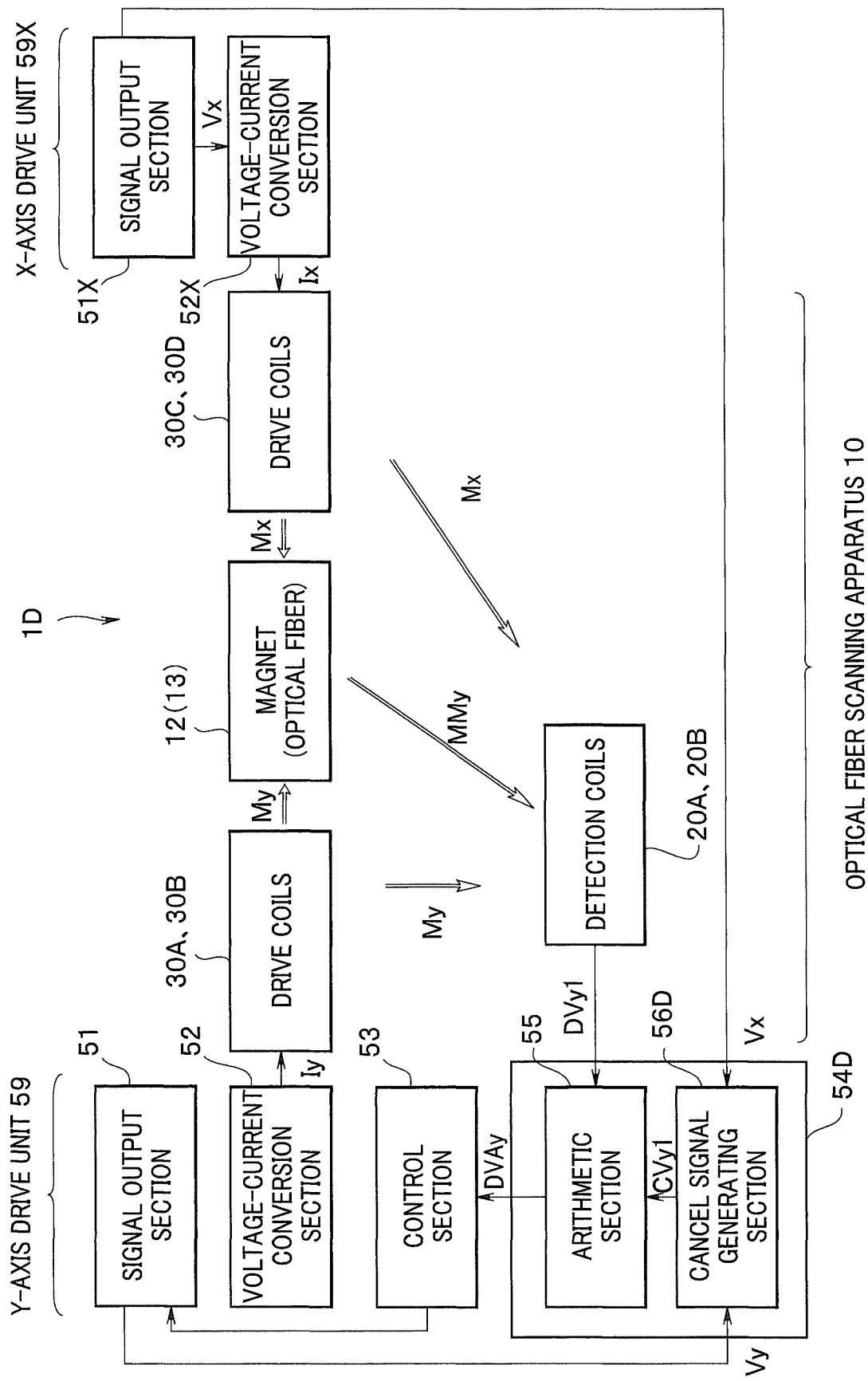
FIG. 12 is a diagram of a configuration of an optical fiber scanning system according to a second embodiment.

As illustrated in FIG. 12, an X-axis direction drive magnetic field Mx generated by drive coils 30C, 30D of a third coil set 43 and a fourth coil set 44 are also applied to detection coils 20A, 20B in the optical fiber scanning system 1D.

If the detection coils 20A, 20B are arranged at respective positions completely orthogonal to the drive coils 30C, 30D, a detection signal DVy of the detection coils 20A, 20B is not affected by variation of a drive magnetic field Mx. However, in the case of an ultra-compact optical fiber scanning apparatus 10, a second drive magnetic field signal (X-axis drive magnetic field signal) DVx2 in response to variation of a drive magnetic field Mx may be contained in a detection signal DVy because of a manufacturing error.

Figure 13:
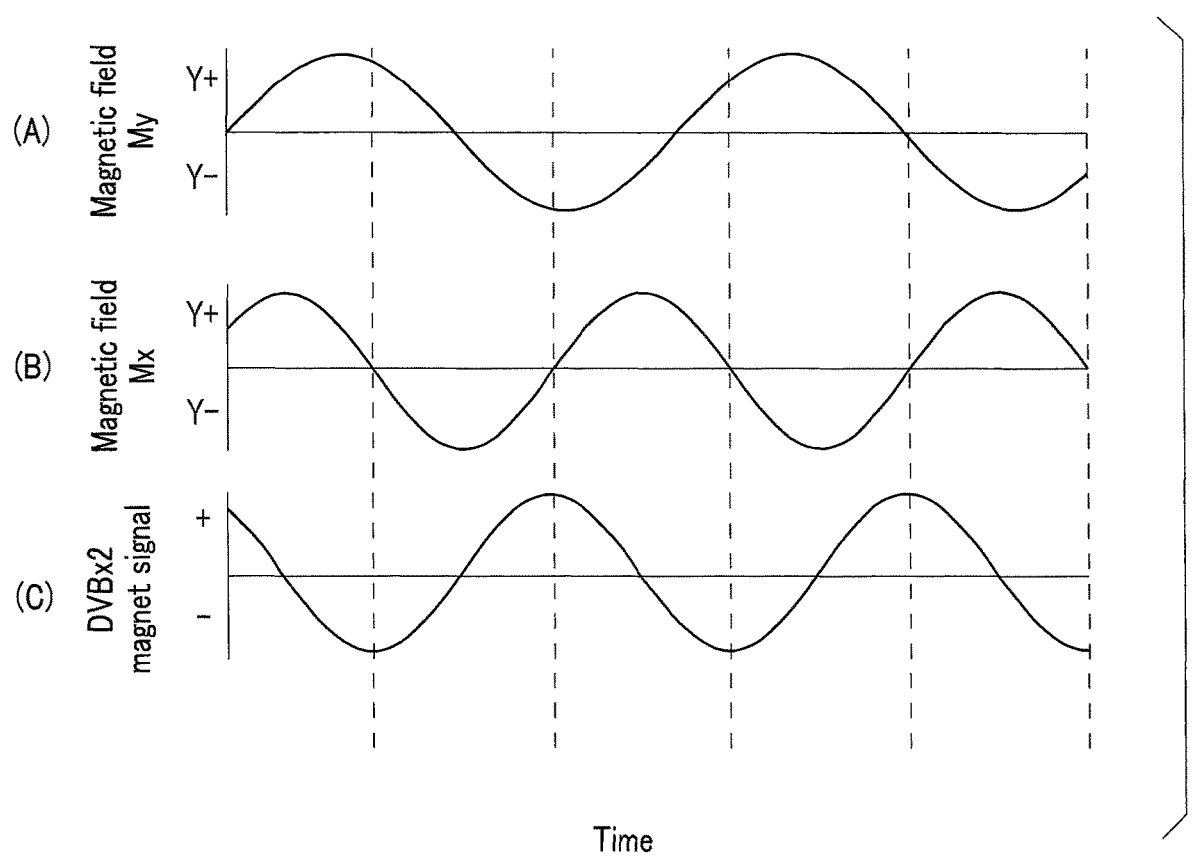
FIG. 13 is a diagram illustrating, e.g., signal waveforms in the optical fiber scanning system according to the second embodiment.

The X-axis direction drive magnetic field Mx indicated in FIG. 13(B) is different in frequency f from the Y-axis direction drive magnetic field My indicated in FIG. 13(A).

FIG. 13(C) indicates a second drive magnetic field signal (X-axis drive magnetic field signal) DVBx2 contained in a detection signal DVy1.

A correction section MD in the optical fiber scanning system 1D also removes the second drive magnetic field signal (X-axis drive magnetic field signal) DVBx2 from the detection signal DVy1.

As illustrated in FIG. 12, a signal output section 51X of the X-axis drive unit 59X in the optical fiber scanning system 1D outputs a drive signal Vx to a voltage-current conversion section 52X for the X-axis direction and outputs the drive signal Vx also to a cancel signal output section 56D of the Y-axis drive unit 59. In order to generate a cancel signal corresponding to the second drive magnetic field signal DVBx2 using the drive signal Vx, the cancel signal output section 56D includes, for example, a differential amplifier including a variable resistor and a capacitor. The drive signal Vx is adjusted so that the detection signal DVy1 becomes zero while a drive power signal Ix is supplied to the X-axis drive unit 59X in a state in which the drive signal Vx is not affected by a magnet 12.

The cancel signal output section 56D in the correction section 54D converts a drive magnetic field signal DVBy1 in which a Y-axis direction drive magnetic field signal DVBy and the X-axis direction drive magnetic field signal DVBx2 are superimposed on each other to a cancel signal CVy1.

An arithmetic section 55 removes the cancel signal CVy1 corresponding to the drive magnetic field signal DVBy in response to variation of the drive magnetic field My and the second drive magnetic field signal (X-axis drive magnetic field signal) DVBx2 in response to variation of the drive magnetic field Mx, from the detection signal DVy1.

Although not illustrated, in the optical fiber scanning system 1D, a drive magnetic field signal DVBy2 in response to variation of the drive magnetic field My generated by the drive coils 30A, 30B of the first coil set 41 and the second coil set 42 is removed from a detection signal outputted by detection coils 20C, 20D of the third coil set 43 and the fourth coil set 44 by the X-axis drive unit 59X.

In the optical fiber scanning system 1D, a cancel signal corresponding to a drive magnetic field signal in response to variation of a drive magnetic field and a second drive magnetic field signal in response to variation of a drive magnetic field generated by orthogonally-arranged drive coils is removed from a detection signal.

Therefore, the optical fiber scanning system 1D enables higher-precision control than the optical fiber scanning system 1.

Third Embodiment

Next, an optical fiber scanning system 1E according to a third embodiment will be described. The optical fiber scanning system 1E is similar to the optical fiber scanning system 1D and has effects that are the same as the effects of the optical fiber scanning system 1D, and thus, components having functions that are the same as the functions of components in the optical fiber scanning system 1D are provided with reference numerals that are the same as reference numerals of the components in the optical fiber scanning system 1D and description of such components will be omitted. Also, as described later, in FIG. 14, illustration of components of an X-axis drive unit 59X, components having not direct relationship with operation of a Y-axis drive unit 59, is omitted.

Figure 14:
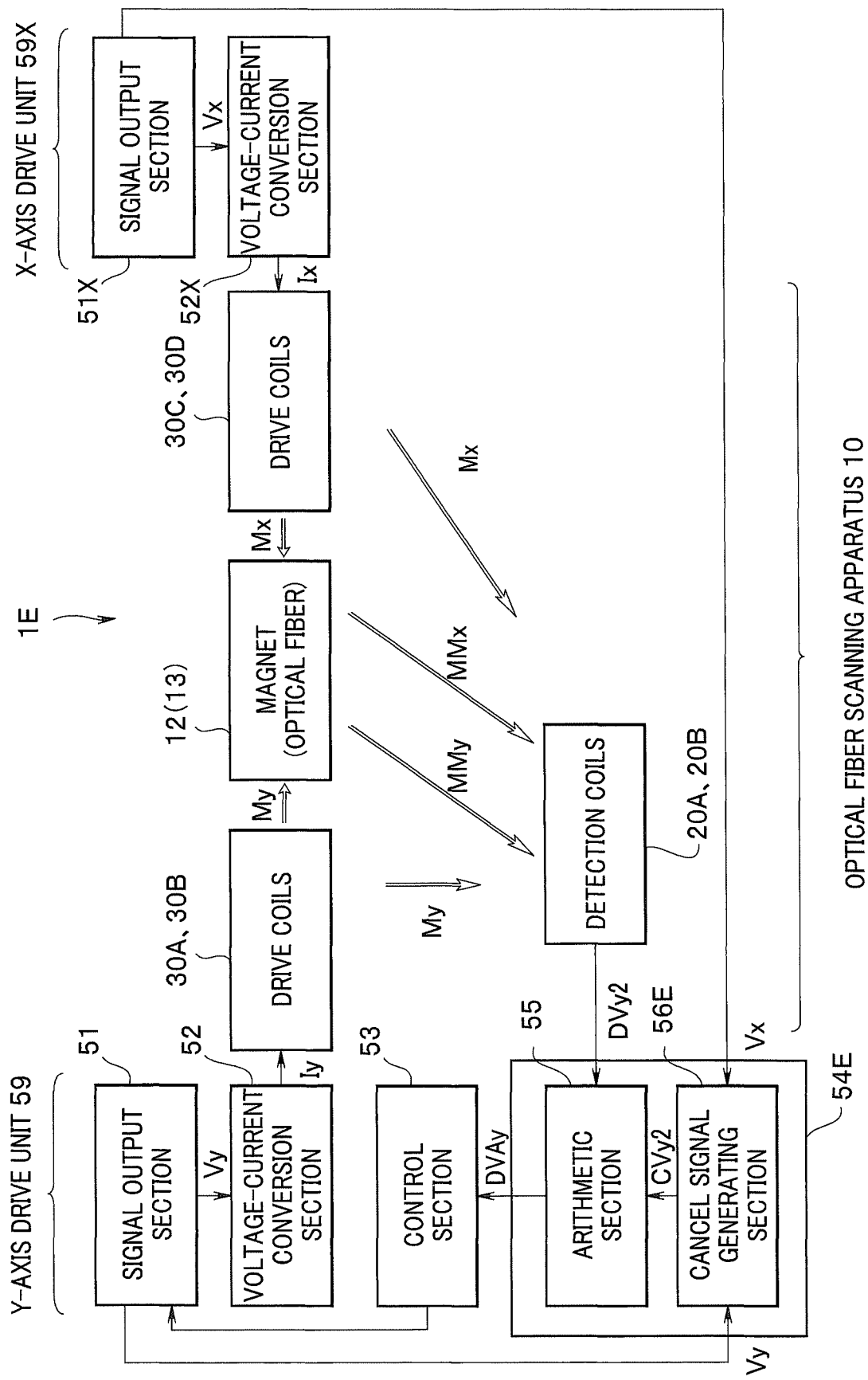
FIG. 14 is a diagram of a configuration of an optical fiber scanning system according to a third embodiment.

As illustrated in FIG. 14, a second magnet magnetic field signal (X-axis magnet magnetic field signal) DVAx2 in response to variation of a magnet magnetic field MMx due to movement (vibration) of a magnet 12 caused by a drive magnetic field Mx generated by drive coils 30C, 30D of a third coil set 43 and a fourth coil set 44 in the optical fiber scanning system 1E is also superimposed on a detection signal.

A correction section 54E outputs a magnet magnetic field signal (Y-axis magnet magnetic field signal) DVAy by removing a second drive magnetic field signal (X-axis drive magnetic field signal) DVx2 and a second magnet magnetic field signal (X-axis magnet magnetic field signal) DVAx2 from a detection signal DVy2.

Figure 15:
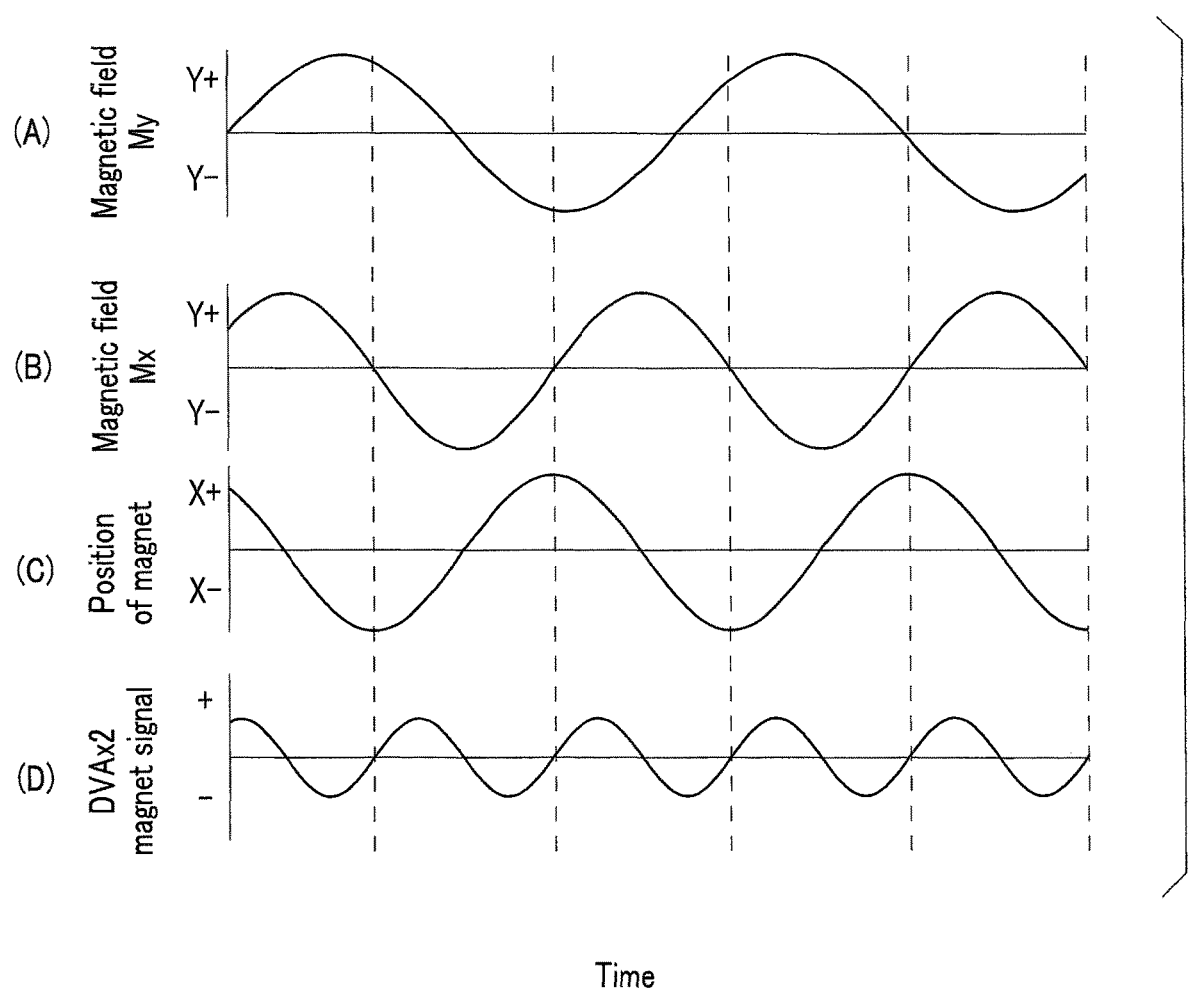
FIG. 15 is a diagram illustrating, e.g., signal waveforms in the optical fiber scanning system according to the third embodiment.

A Y-axis direction drive magnetic field My, which is illustrating in FIG. 15(A), is different in frequency f from an X-axis direction drive magnetic field Mx, which is illustrated in FIG. 15(B). As illustrated in FIG. 15(C), the drive magnetic field Mx causes the magnet 12 to vibrate in the X-axis direction.

The detection coils 20A, 20B generate a magnet magnetic field signal DVAx2 in response to variation of a magnet magnetic field where the drive magnetic field Mx causes the magnet 12 to vibrate in the X-axis direction. As illustrated in FIG. 15(E), a cycle of the magnet magnetic field signal DVAx2 is twice a cycle of the drive magnetic field Mx.

A cancel signal output section 56E in a correction section 54E can remove the second magnet magnetic field signal DVAx2 from the detection signal DVy1, for example, using a frequency filter.

Likewise, a correction section in the X-axis drive unit 59X can remove a second magnet magnetic field signal DVAy2 from a detection signal using a frequency filter.

In other words, in the optical fiber scanning system 1E, a drive magnetic field signal in response to variation of a drive magnetic field, a second drive magnetic field signal in response to variation of a drive magnetic field generated by orthogonally-arranged drive coils and a second magnet magnetic field signal in response to vibration of a magnet caused by a drive magnetic field generated by the orthogonally-arranged drive coils can be removed from a detection signal.

Therefore, the optical fiber scanning system 1E enables higher-precision control than the optical fiber scanning systems 1, 1D.

Fourth Embodiment

Next, an endoscope system 9 according to a fourth embodiment, which includes any one of the optical fiber scanning systems 1, 1A to 1E, will be described.

Figure 16:
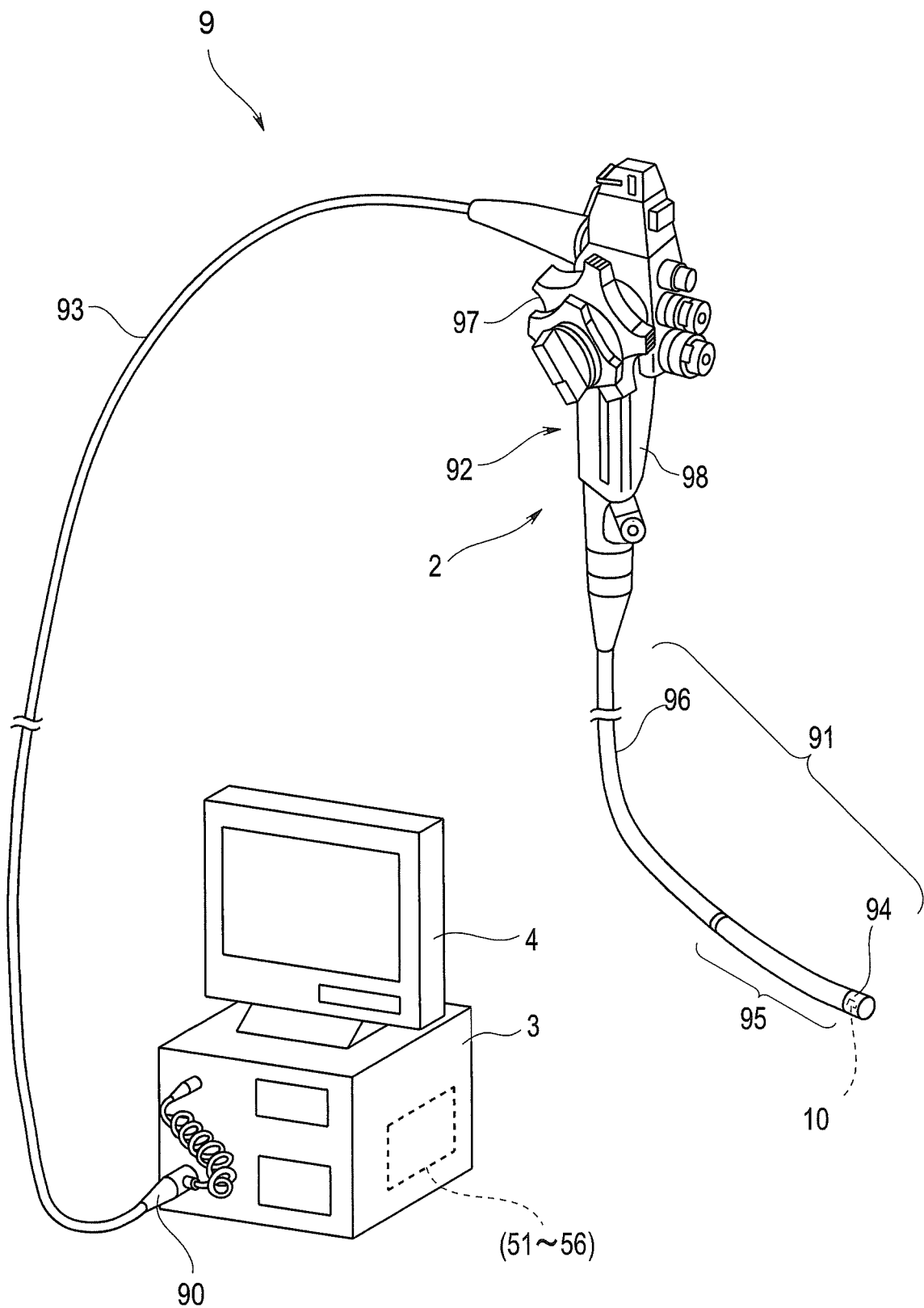
FIG. 16 is a perspective view of an endoscope system including an optical fiber scanning system according to a fourth embodiment.

An endoscope 2, which is illustrated in FIG. 16, is an optical scanning-type endoscope includes the already-described optical fiber scanning apparatus 10 in a rigid distal end portion 94 of an insertion portion 91.

The endoscope system 9 includes the endoscope 2, a main body 3 and a monitor 4. The endoscope 2 irradiates a subject with illuminating light while causing the illuminating light to two-dimensionally scan by means of the optical fiber scanning apparatus 10, detects reflected light (return light) from the subject, performs data processing in the main body 3 and displays a generated subject image on the monitor 4.

The endoscope 2 includes an elongated insertion portion 91 to be inserted into a living body, an operation portion 92, and a universal cable 93 in which an electrical cable, etc., are inserted. The insertion portion 91 of the endoscope 2 includes a rigid distal end portion 94, a bending portion 95 and a flexible tube portion 96. Here, the endoscope 2 according to the embodiment is what is called a flexible endoscope, but even if the endoscope 2 is what is called a rigid endoscope including a rigid insertion portion 91, the endoscope 2 has the later-described effects.

In the operation portion 92, a bending operation knob 97 to be operated to bend the bending portion 95 is disposed. The part of joining between the insertion portion 91 and the operation portion 92 is a grasping portion 98 to be grasped by a user.

The universal cable 93 provided so as to extend from the operation portion 92 is connected to the main body 3 via a connector 90. The main body 3 is connected to the monitor 4 configured to display an endoscopic image.

Figure 17:
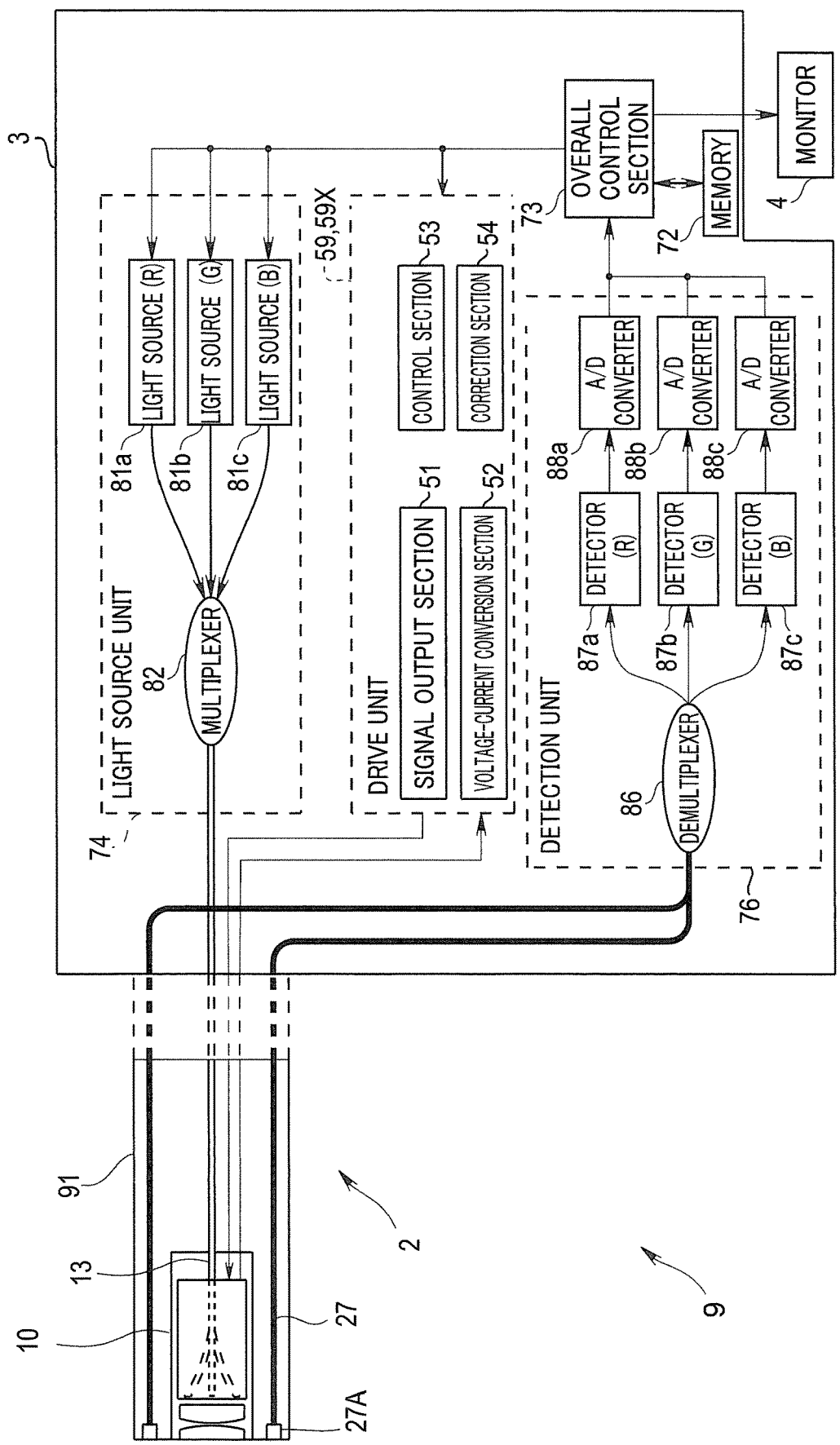
FIG. 17 is a diagram of a configuration of the endoscope system including the optical fiber scanning system according to the fourth embodiment.

Next, FIG. 17 illustrates a configuration of the endoscope system 9.

Inside the insertion portion 91 of the endoscope 2, a detection fiber 27 inserted from the proximal end side to the distal end side along an inner periphery of the insertion portion 91 and configured to guide reflected light from a subject is provided. A detection optical system 27A is disposed at a distal end of the detection fiber 27. As a result of the connector 90 of the endoscope 2 being connected to the main body 3, the detection fiber 27 is connected to a demultiplexer 86.

The main body 3 includes drive units 59, 59X, a memory 72, an overall control section (overall controller) 73, a light source unit 74 and a detection unit 76. The light source unit 74 includes three light sources 81a, 81b, 81c and a multiplexer 82.

As described with reference to FIG. 6, the drive units 59, 59X include signal output sections 51, 51X, voltage-current conversion sections 52, 52X, control sections 53, 53X and correction sections 54, 54X, respectively.

In the memory 72, e.g., a control program for overall control of the main body 3 is stored.

The overall control section 73 reads the control program from the memory 72 and performs control of the light source unit 74 and the drive units 59, 59X. Also, the overall control section 73 performs control to perform data processing of a light intensity signal of reflected light from a subject, which has been detected by the detection unit 76, and cause a resulting image to be displayed on the monitor 4.

The light sources 81a, 81b, 81c of the light source unit 74 emit respective light rays of different wavelength bands, for example, light rays of R (red), G (green) and B (blue) wavelength bands to the multiplexer 82, under the control of the overall control section 73. The multiplexer 82 multiplexes the light rays of the R, G and B wavelength bands and outputs the resulting light to the optical fiber 13.

The drive units 59, 59X each output a drive power signal for causing the distal end of the optical fiber 13 of the optical fiber scanning apparatus 10 to scan in a desired scanning method to the respective drive coils 30 under the control of the overall control section 73. In other words, the drive units 59, 59X each output a predetermined drive power signal to the respective coil sets 40 of the optical fiber scanning apparatus 10 so as to drive the distal end of the optical fiber 13 leftward/rightward (X-axis direction) and upward/downward (Y-axis direction) relative to an insertion axis (Z-axis) of the insertion portion 91.

The detection fiber 27 receives light reflected by a surface of a subject and guides the received reflected light to the demultiplexer 86. The demultiplexer 86 is, for example, a dichroic mirror, and demultiplexes the reflected light into respective predetermined wavelength bands. More specifically, the demultiplexer 86 demultiplexes the reflected light guided by the detection fiber 27 into reflected light rays of the R, G and B wavelength bands and outputs the resulting reflected light rays to the respective detectors 87a, 87b, 87c.

The detectors 87a, 87b and 87c are, e.g., PD elements configured to detect light intensities of the reflected light rays of the R, G and B wavelength bands, respectively. The light intensity signals detected by the detectors 87a, 87b and 87c are outputted to the A/D converters 88a, 88b, 88c, respectively. The A/D converters 88a to 88c convert the light intensity signals outputted from the detectors 87a to 87c, respectively, from analog signals to digital signals and outputs the digital signals to the overall control section 73.

The overall control section 73 subjects the digital signals from the A/D converters 88a to 88c to predetermined image processing to generate a subject image and displays the subject image on the monitor 4.

Here, as the illuminating light, monochromatic light may be used or laser light may be used.

The optical scanning-type endoscope 2 includes any one of the thin optical fiber scanning apparatuses 10, 10A to 10K each configured to perform efficient scanning irradiation, in the rigid distal end portion 94 of the insertion portion 91, and thus, the rigid distal end portion 94 is thin and less invasive. Also, the optical fiber scanning apparatuses 10, 10A to 10K performs high-precision scanning irradiation, and thus, the optical scanning-type endoscope 2 can provide a better image. Also, the optical scanning-type endoscope 2 consumes less power because the optical fiber scanning apparatuses 10, 10A to 10K can be driven efficiently.

It should be understood that: the present invention is not limited to the above-described embodiments; and various changes, combinations and applications are possible without departing from the spirit of the invention.

What is claimed is:

1. An optical fiber scanning system comprising an optical fiber scanning apparatus and a drive unit, wherein:
   the optical fiber scanning apparatus includes
   an optical fiber on which a magnet is disposed, the optical fiber being arranged along a center axis of a tubular casing and configured to output light from a free end;
   four drive coils configured to apply a drive magnetic field generated using an inputted drive power signal to the magnet to drive the free end of the optical fiber; and
   four detection coils configured to output a detection signal that is an induced electromotive force signal in response to variation of a magnetic field;
   the drive unit includes
   a signal output circuit configured to output a drive signal subjected to voltage control,
   a voltage-current conversion circuit configured to convert the drive signal to the drive power signal subjected to current control and output the drive power signal,
   a controller configured to perform feedback control of the drive power signal, and
   a correction circuit configured to output a magnet magnetic field signal in response to variation of a magnet magnetic field due to movement of the magnet, by removing a drive magnetic field signal in response to variation of the drive magnetic field, from the detection signal;
   four coil sets each including any of the drive coils and any of the detection coils are disposed at respective positions that are rotationally symmetric with respect to the optical fiber;
   the correction circuit outputs the magnet magnetic field signal by removing the drive magnetic field signal from the detection signal; and
   the controller is configured to control the signal output circuit based on the magnet magnetic field signal.

2. The optical fiber scanning system according to claim 1, wherein each of the drive coils and the detection coils is a planar spiral coil.

3. The optical fiber scanning system according to claim 2, wherein:
   each of the drive coils of two coil sets arranged so as to face each other from among the coils sets is serially connected;
   each of the detection coils of the two coil sets arranged so as to face each other is serially connected, and each of the detection signals outputted by the two detection coils serially connected is added up and outputted as an added-up detection signal; and
   the correction circuit outputs the magnet magnetic field signal by removing the drive magnetic field signal from the added-up detection signal.

4. The optical fiber scanning system according to claim 3, wherein the correction circuit includes a cancel signal generation circuit configured to convert the drive signal to a cancel signal and output the cancel signal and the correction circuit is configured to output the magnet magnetic field signal based on the added-up detection signal and the cancel signal.

5. The optical fiber scanning system according to claim 4, wherein the cancel signal generation circuit is configured to be set so that the magnet magnetic field signal is zero in a state in which the magnet does not move.

6. The optical fiber scanning system according to claim 5, wherein the correction circuit includes a phase adjustment circuit configured to generate the cancel signal subjected to phase adjustment.

7. The optical fiber scanning system according to claim 1, wherein the correction circuit includes an integration circuit configured to integrate the magnet magnetic field signal and output a position signal indicating a position of the magnet.

8. The optical fiber scanning system according to claim 3, wherein:
the four coil sets include a first coil set and a second coil set arranged so as to face each other and a third coil set and a fourth coil set arranged so as to face each other; and
the correction circuit is configured to remove a second drive magnetic field signal in response to variation of the drive magnetic field generated by the drive coils of the third coil set and the fourth coil set from the detection signal outputted by the detection coils of the first coil set and the second coil set.

9. The optical fiber scanning system according to claim 8, wherein the correction circuit is configured to remove a second magnet magnetic field signal in response to variation of the magnet magnetic field due to movement of the magnet caused by the drive magnetic field generated by the third coil set and the fourth coil set.

10. The optical fiber scanning system according to claim 1, wherein the drive signal is a sine-wave signal.

11. An endoscope system comprising an optical fiber scanning apparatus of an optical fiber scanning system in a distal end rigid portion of an insertion portion of an endoscope, the optical fiber scanning system including an optical fiber scanning apparatus and a drive unit, wherein:
the optical fiber scanning apparatus includes
an optical fiber on which a magnet is disposed, the optical fiber being arranged along a center axis of a tubular casing and configured to output light from a free end;
four drive coils configured to apply a drive magnetic field generated using an inputted drive power signal to the magnet to drive the free end of the optical fiber; and
four detection coils configured to output a detection signal that is an induced electromotive force signal in response to variation of a magnetic field;
the drive unit includes
a signal output circuit configured to output a drive signal subjected to voltage control,
a voltage-current conversion circuit configured to convert the drive signal to the drive power signal subjected to current control and output the drive power signal,
a controller configured to perform feedback control of the drive power signal, and
a correction circuit configured to output a magnet magnetic field signal in response to variation of a magnet magnetic field due to movement of the magnet, by removing a drive magnetic field signal in response to variation of the drive magnetic field, from the detection signal;
four coil sets each including any of the drive coils and any of the detection coils are disposed at respective positions that are rotationally symmetric with respect to the optical fiber;
the correction circuit outputs the magnet magnetic field signal by removing the drive magnetic field signal from the detection signal; and
the controller is configured to control the signal output circuit based on the magnet magnetic field signal.

* * * * *